(12) United States Patent
Mayer

(10) Patent No.: US 12,178,484 B2
(45) Date of Patent: Dec. 31, 2024

(54) MAXILLOMANDIBULAR FIXATION DEVICE

(71) Applicant: Peter J. Mayer, Duluth, MN (US)

(72) Inventor: Peter J. Mayer, Duluth, MN (US)

( * ) Notice: Subject to any disclaimer, the term of this patent is extended or adjusted under 35 U.S.C. 154(b) by 817 days.

(21) Appl. No.: 17/263,930

(22) PCT Filed: Jul. 18, 2019

(86) PCT No.: PCT/US2019/042423
§ 371 (c)(1),
(2) Date: Jan. 28, 2021

(87) PCT Pub. No.: WO2020/046491
PCT Pub. Date: Mar. 5, 2020

(65) Prior Publication Data
US 2022/0168031 A1   Jun. 2, 2022

Related U.S. Application Data

(60) Provisional application No. 62/724,188, filed on Aug. 29, 2018.

(51) Int. Cl.
*A61B 17/80* (2006.01)
*A61B 17/86* (2006.01)
(Continued)

(52) U.S. Cl.
CPC .......... *A61B 17/8071* (2013.01); *A61B 17/86* (2013.01); *A61C 7/28* (2013.01); *A61C 7/36* (2013.01)

(58) Field of Classification Search
CPC .. A61C 5/007; A61C 5/80; A61C 7/28; A61C 7/287; A61C 7/30; A61C 7/34; A61C 7/14; A61C 7/18; A61C 7/22; A61C 7/12; A61C 7/143; A61C 7/36; A61F 5/05891; A61F 5/058; A61B 17/8071
(Continued)

(56) References Cited

U.S. PATENT DOCUMENTS 2,086,656 A * 7/1937 Woodward .......... A61F 5/05891
602/5
2,481,177 A * 9/1949 Tofflemire ............... A61C 7/00
602/5
(Continued)

FOREIGN PATENT DOCUMENTS

WO   WO-2016/007415 A2   1/2016

OTHER PUBLICATIONS

International Search Report and Written Opinion mailed Oct. 2, 2019, for related application No. PCT/US2019/042423, 12 pages.
(Continued)

*Primary Examiner* — Nicholas D Lucchesi
(74) *Attorney, Agent, or Firm* — Fox Rothschild LLP

(57) ABSTRACT

A maxillomandibular fixation device is provided. The maxillomandibular fixation device broadly includes a strip of material for positioning around an individual's teeth; an arch bar positioned against the teeth; and a clamping assembly for clamping the material to the arch bar. The material may include a single length of material or may be multiple lengths of shorter material. The clamping assembly may include a lever portion and a hook portion or may be a single slidable side clamp.

16 Claims, 16 Drawing Sheets

(51) Int. Cl.
*A61C 7/28* (2006.01)
*A61C 7/36* (2006.01)

(58) Field of Classification Search
USPC .............................. 433/23, 19, 8, 10, 18, 24
See application file for complete search history.

(56) References Cited

U.S. PATENT DOCUMENTS

| | | | | |
|---|---|---|---|---|
| 2,502,902 | A * | 4/1950 | Tofflemire | A61F 5/05891 |
| | | | | 606/57 |
| 3,091,856 | A * | 6/1963 | Goldstein | A61C 7/00 |
| | | | | 433/18 |
| 4,202,328 | A * | 5/1980 | Sukkarie | A61F 5/05891 |
| | | | | 433/18 |
| 4,230,104 | A | 10/1980 | Richter | |
| 4,813,869 | A * | 3/1989 | Gatewood | A61C 5/007 |
| | | | | 606/103 |
| 5,039,303 | A * | 8/1991 | Irwin | A61C 7/00 |
| | | | | 433/215 |
| 5,613,853 | A * | 3/1997 | Chasan | A61C 5/007 |
| | | | | 433/215 |
| 5,829,979 | A | 11/1998 | Kobashigawa et al. | |
| 6,089,861 | A | 7/2000 | Kelly et al. | |
| 6,257,884 | B1 | 7/2001 | Chang | |
| 8,500,445 | B2 * | 8/2013 | Borri | A61C 7/20 |
| | | | | 433/18 |
| 2002/0068254 | A1 | 6/2002 | Campbell | |
| 2005/0277084 | A1 | 12/2005 | Cinader et al. | |
| 2005/0282115 | A1 | 12/2005 | Gedebou | |
| 2009/0148804 | A1 * | 6/2009 | Marcus | A61B 17/60 |
| | | | | 433/7 |
| 2010/0124727 | A1 | 5/2010 | Shah et al. | |
| 2011/0288551 | A1 | 11/2011 | Walther et al. | |
| 2013/0295517 | A1 | 11/2013 | Singer et al. | |
| 2014/0134564 | A1 | 5/2014 | Baker | |
| 2014/0238435 | A1 | 8/2014 | Ewing | |
| 2015/0351801 | A1 | 12/2015 | Montejo | |
| 2016/0051384 | A1 | 2/2016 | Patel et al. | |
| 2018/0221069 | A1 | 8/2018 | Kohler et al. | |

OTHER PUBLICATIONS

International Search Report and Written Opinion mailed Jun. 21, 2019, for related application No. PCT/US2019/025732, 9 pages.

* cited by examiner

MAXILLOMANDIBULAR FIXATION DEVICE

FIELD OF THE INVENTION

The invention is generally related to maxillomandibular fixation dental devices. More particularly the invention relates to a single strip of material for positioning around an individual's teeth in combination with a clamping assembly for securing the single strip of material to an arch bar.

BACKGROUND OF THE INVENTION

When treating facial bone (maxilla and/or mandible) fractures, the number one goal is to align the teeth such that, when the bones heal, the patient's bite is properly aligned. As seen in the prior art device depicted in FIG. 1, for many years the technique was to place a 0.5 mm×3 mm strip of stainless steel, with hooks on it, along the buccal (cheek side) aspect of the gums in the maxilla and mandible. These "arch bars" would be secured using stainless steel wires wrapped around each individual tooth and then around the arch bar. The wires would then be twisted, cut and bent to avoid any sharp edges of the wires poking into the mucosa. After this was completed in the upper (maxilla) and lower (mandible) arches, wires would wrap around the upper and lower arch bar hooks resulting in the jaws being wired shut. This could either be the definitive treatment, the result of which would be healing of the bones in the proper position, or allow for metal plates to be placed, fixating the fracture segments. However, the disadvantages of this technique are numerous. It is a technically demanding procedure for a surgeon with results varying depending on the level of skill of the surgeon. The procedure also requires a significant amount of time to complete, which is demanding on both the surgeon and the patient. Damage to the mucosa and periodontal bone is frequently encountered with instability over time due to stretching of the wires. Further instability results if the patient is missing teeth.

Another conventional method of wiring the jaws shut is seen in FIG. 2. Screws are placed in the maxilla and mandible, through the mucosa. The protruding screws then act as a "hook" to wrap wires around. Disadvantages are also associated with this technique. Damage to tooth roots may result in occasional tooth loss. Loosening of the screws over time resulting in instability of the maxillomandibular fixation. Overgrowth of the mucosa over the screws causing pain and the need for surgical removal of the maxillomandibular fixation.

A third, more recent method of maxillomandibular fixation seen in FIG. 3 is to use an extramucosal plate containing hooks, secured by transmucosal screws. The disadvantages of this technique are damage to tooth roots, loosening of the screws over time resulting in maxillomandibular fixation instability and overgrowth of the mucosa over the plate and screws causing pain and the need for surgical removal.

Therefore, what is needed are new and improved devices for maxillomandibular fixation that addresses the foregoing problems.

BRIEF SUMMARY OF THE INVENTION

A maxillomandibular fixation device is provided. The maxillomandibular fixation device broadly includes a single strip of material for positioning around an individual's teeth; an arch bar positioned against the teeth; and a clamping assembly for clamping the material to the clamping assembly. The strip of material may include a single length of material from 45 cm to 50 cm or may include a plurality of strips of material from 3 cm to 4 cm in length.

The arch bar may include a projection extending from a surface thereof and include an upper track and a lower track. Alternatively, the arch bar may include one or more hooks thereon.

The clamping assembly may comprise a single clamping assembly or include a plurality of clamping assemblies. The clamping assembly may include a base having a hook coupled to a lower portion thereof and a clamp portion positioned thereon. The hook may be integrally molded to the clamping assembly or may simply be coupled to the clamping assembly.

The clamping assembly may include a lever moveable between a first open position and a second closed position. In the second closed position, the lever immovably secures the strip of material in position. The lever may be positioned on an upper portion of the clamping assembly or on a side portion.

The clamping assembly may include a projection extending from a side surface that includes a mating surface thereon that mates with the hook on the arch bar such that when the clamping assembly is slidingly received by the arch bar the mating surface matingly snaps into place with the hook.

Alternatively, the clamping assembly may include a removable insert that secures the material in place by a ratcheting friction fit.

The maxillomandibular fixation device may include a strip of material for positioning around an individual's teeth; an arch bar positioned against the teeth; and a clamping assembly for clamping the material to the clamping assembly.

The maxillomandibular fixation device may include a single strip of material for positioning around an individual's teeth; a single clamping assembly for securing the material to the clamping assembly, the clamping assembly including one or more openings therethrough; and an arch bar received by at least one of the openings in the clamping assembly.

The maxillomandibular fixation device may include a single strip of material for positioning around an individual's teeth; a single clamping assembly for securing the material to the clamping assembly, the clamping assembly including a base having a channel on a backside thereof and an indentation on a front portion thereof, the base further including a lever on a side thereof, the lever moveable between a first position and a second position; an arch bar including a body and a plurality of hooks, the body received by the channel in the clamping assembly. The base may include a laterally extending U-shaped projection defining a U-shaped space wherein one of the arch bar hooks matingly receives the U-shaped space in a snap fit relationship.

The maxillomandibular fixation device may include a single strip of material for positioning around an individual's teeth; a single clamping assembly for securing the material to the clamping assembly, the clamping assembly including a base having a channel on a backside thereof an opening extending therethrough, the backside of the opening including a ratcheting surface wholly or partially extending around a circumference thereof; a spool received within the opening; and an arch bar including a body and a plurality of hooks, the body received by the channel in the clamping assembly.

These and other features of the maxillomandibular fixation device in accordance with the invention will now be described.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
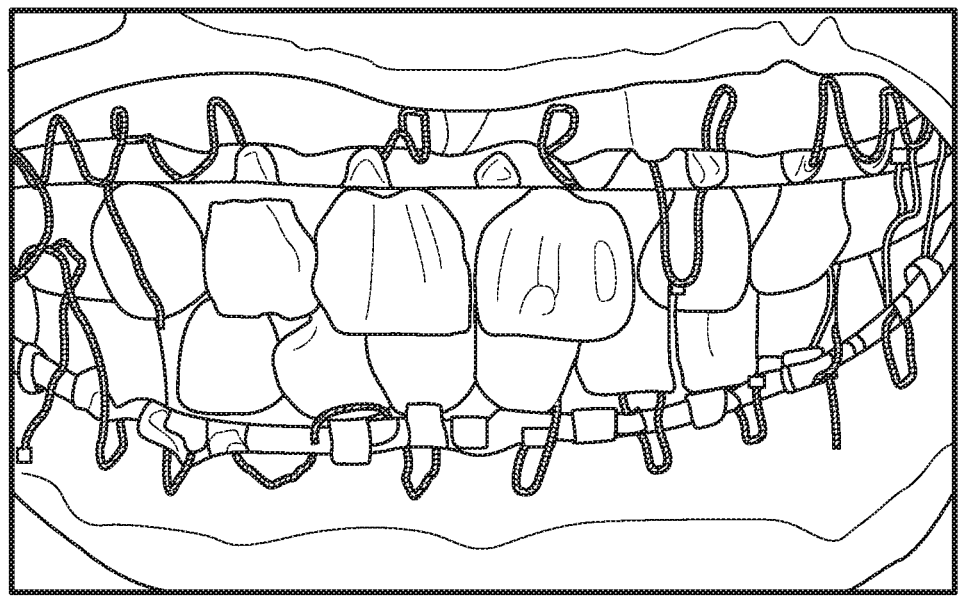
FIG. 1 is a conventional maxillomandibular fixation device.
Figure 2:
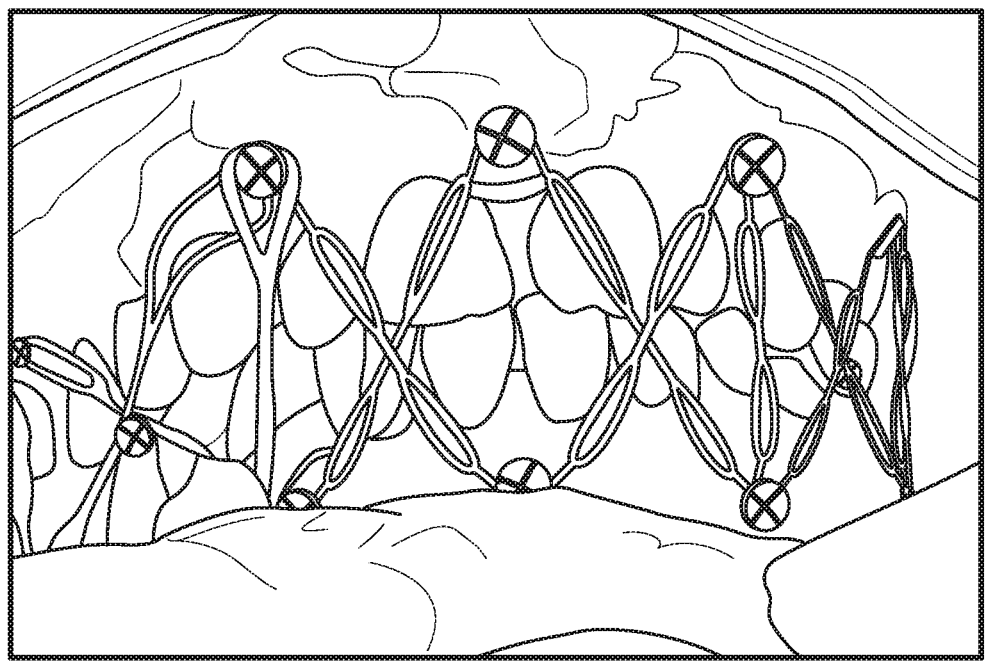
FIG. 2 is a second conventional maxillomandibular fixation device.
Figure 3:
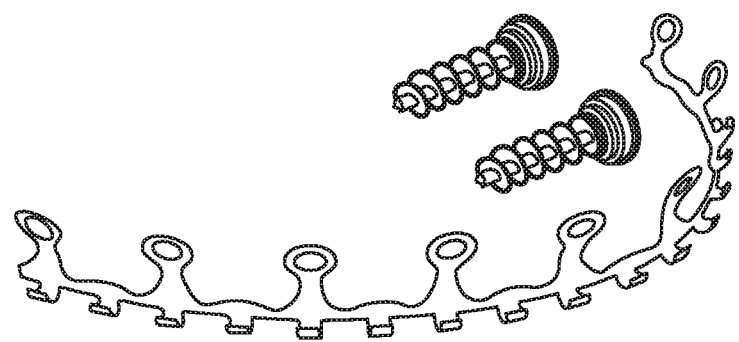
FIG. 3 is a third conventional maxillomandibular fixation.
Figure 4:
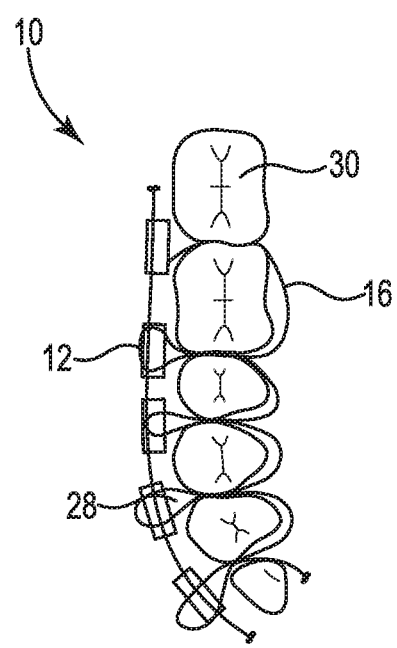
FIG. 4 is a top view of a maxillomandibular fixation device in one aspect of the invention.
Figure 5:
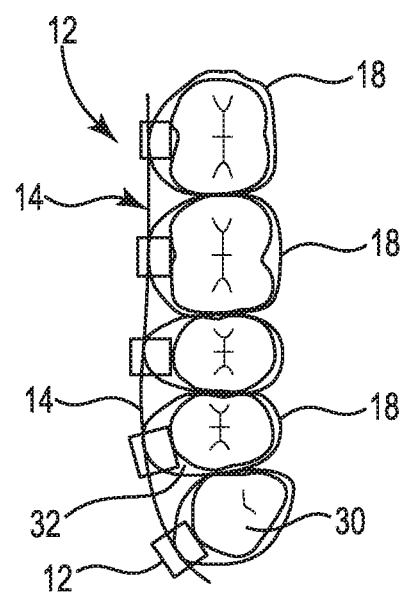
FIG. 5 is top view of the maxillomandibular fixation device in another aspect of the invention.

Referring now to FIGS. 4-8 one aspect of a maxillomandibular fixation device 10 in accordance with an aspect of the invention will now be described. The maxillomandibular fixation device 10 overcomes many of the problems associated with conventional devices and broadly includes a clamp assembly 12, an arch bar 14 for receiving the clamp assembly 12 and a strip of material 16 that wraps around one or more teeth and is clamped in placed by a clamp assembly. Rather than using wires to secure the device around the teeth, the maxillomandibular fixation device 10 uses a single strip of material 16 having a length of approximately 45-50 cm and a width of approximately 2-3 mm. The material may be constructed of an aramid such as KEVLAR (poly-para-phenylene terephthalamide), NOMEX, TECHNORA, an ultra high-density polyethylene (UHDPE), DYNEEMA, or a metal such as stainless steel. Other materials known to those of skill in the art may also be used. In one aspect the material 16 is weaved in and out, between the teeth as best seen in FIG. 4. In another aspect, a shorter strip of material 18 having a length of approximately 3-4 cm and a width of approximately 2-3 mm may be used and individual strips would be wrapped around each tooth as best seen in FIG. 5.

During placement of the device 10, the embrasure space will be entered from the occlusal aspect, avoiding necrosis of the dental papilla as well as greatly speeding up the placement.

Figure 6:
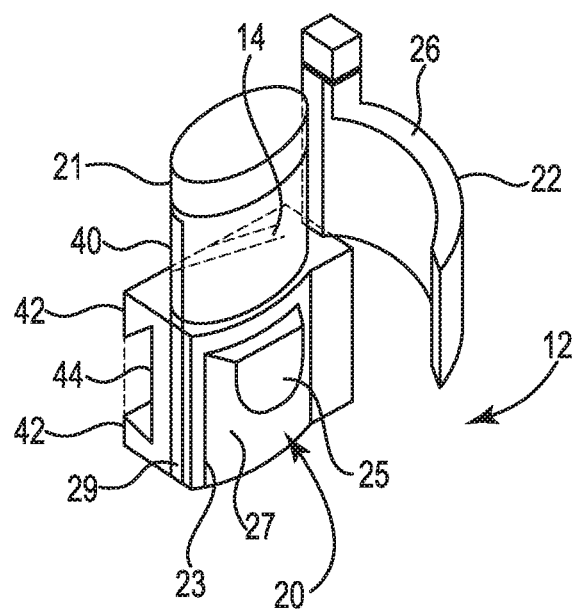
FIG. 6 is a perspective view of a clamp assembly in accordance with the invention.
Figure 8:
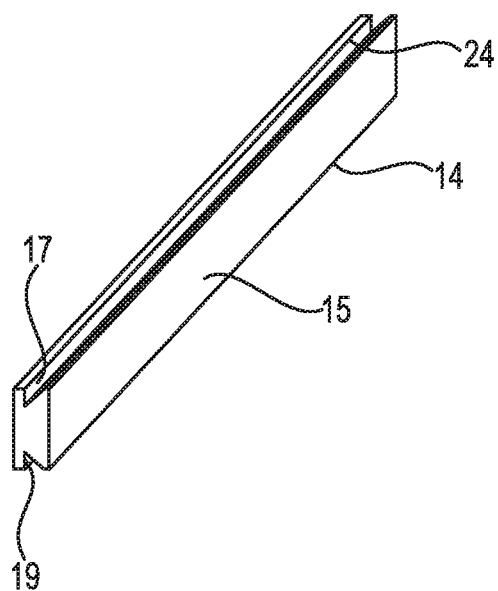
FIG. 8 is perspective view of an arch bar in accordance with one aspect of the invention that receives the clamp assembly.
Figure 12:
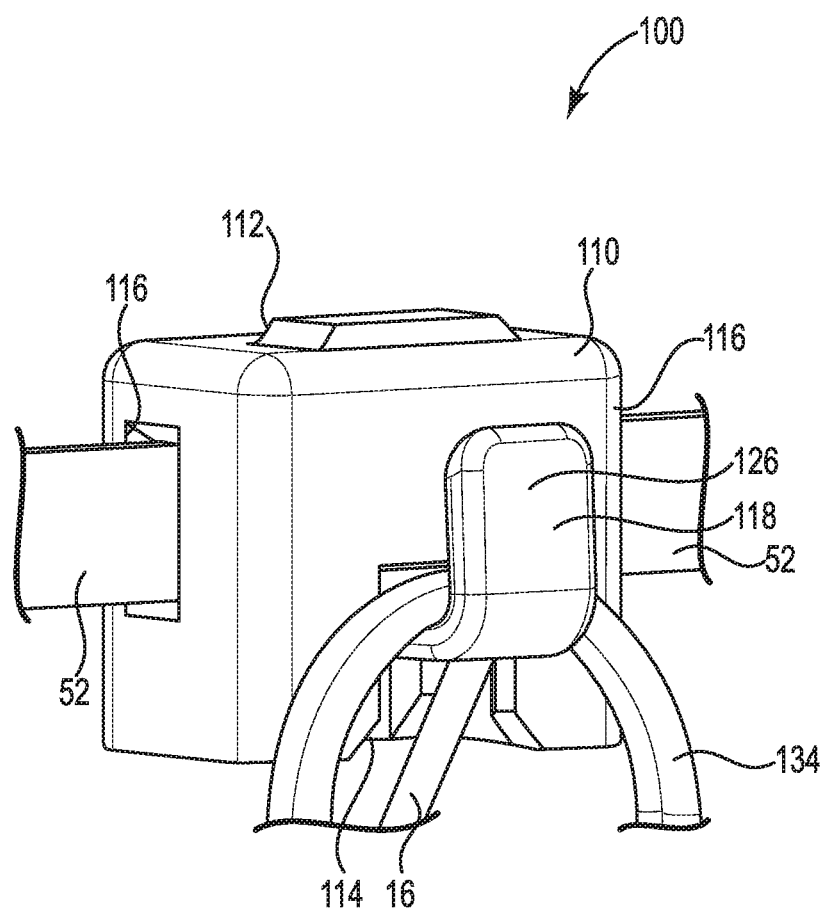
FIG. 12 is a perspective view of another aspect of the clamping assembly in accordance with the invention.

Referring now to FIG. 6, the strip of material 16, 18 is secured to a clamp assembly 12 moveably attached to an arch bar 14 constructed of stainless steel or titanium as best seen in FIG. 8. The clamp assembly 12 includes a base 20 having an upper portion 21 and a lower portion 23. The upper portion 21 and lower portion 23 may be integrally formed or may comprise separate pieces fastened together with fastening means such as adhesive, chemical bonding and the like. The lower portion includes a tab or hook 25 on a first surface and a pair of lips 42 that define a channel 44 therebetween on a second surface 29 of the lower portion 23 of base 20. Hook 25 receives wires 134 (as best seen in FIGS. 12 and 14 A-B) that are used to wire the jaw closed until the healing process finishes. The upper portion 21 of the base 20 includes a clamp 22 having lever 26 that moves from an open position (as shown in FIG. 6) to a closed position which abuts the upper portion 21. Upper portion 21 also includes an aperture 40 that extends through the clamp assembly. Material 16 is threaded through the aperture. In operation, when the lever 26 is moved to the closed position it secures the material 16 in place by compression or a friction fit. Those of skill in the art will appreciate that although a lever 25 is shown other devices and inserts are contemplated so long as they secure the material 16 in place. For example, lever 26 could be eliminated and a separate piece insert used, which would be inserted into the clamp assembly through the aperture. In addition, aperture 40 need not be on the upper portion 21 of the clamp assembly 12 but may be placed anywhere in the clamp assembly so long as the material 16 can be threaded through the clamp assembly.

As seen in FIG. 8, one aspect of arch bar 14 includes a projection 15 on one side thereof, the projection 15 defining upper 17 and lower 19 tracks or channels. The channel 44 of the clamp assembly slidingly and matingly receives projection 15 of the arch bar 14. Channel 44 is shown as having an open configuration defined by a pair of lips 42 but those of skill in the art will appreciated that the pair of lips 42 may also have a closed configuration that defines channel 44, as shown in dashed line. The clamp assembly 12, in the closed position, will both secure the strip of material 16, 18 by compression fit as well as lock the assembly 12 to the upper and lower tracks 17, 19 of the arch bar 14. In another aspect of the device, the clamp 22 may secure the strip of material 16, 18 with the clamp hook assembly 12 movably received by upper and lower channels 17, 19 of arch bar 14. The clamp assembly 12 would be positioned in the embrasure space 28 of the teeth 30 as best seen in FIG. 4 when using the long strip of material 16. Alternatively, if using individual strips of material 18 as seen in FIG. 5, the clamp assembly 12 would be positioned against the buccal aspect 32 of each tooth 30.

Figure 7:
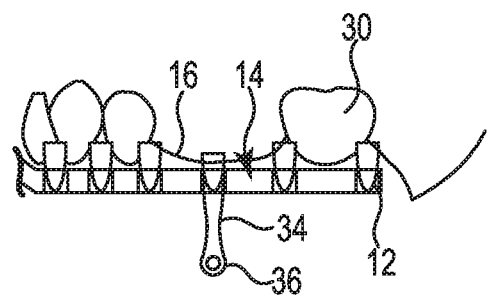
FIG. 7 is a side view of the maxillomandibular fixation device in accordance with the invention.

Referring now to FIG. 7, in edentulous areas an arm 34 that is coupled to and projects radially downward from arch bar 14 can be attached with an area for a bone screw 36 to be placed in the alveolar bone. Those of skill in the art will appreciate that the arm 34 may be coupled to the arch bar 12 by the clamp and hook assembly 12 or by other means known to those of skill in the such as fasteners, screws and the like. Because there is no tooth in the area, no roots will be damaged. The arch bar 14, as seen in FIG. 8, will have been adapted along the buccal aspect of the alveolar arches.

Figure 9:
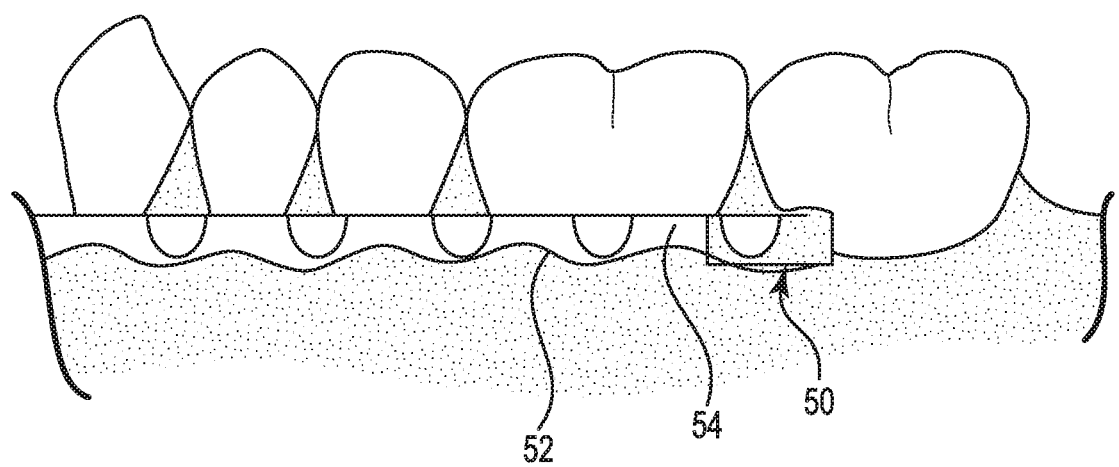
FIG. 9 is a perspective view of another aspect of the maxillomandibular fixation device in accordance with the invention showing a side clamp assembly.
Figure 10:
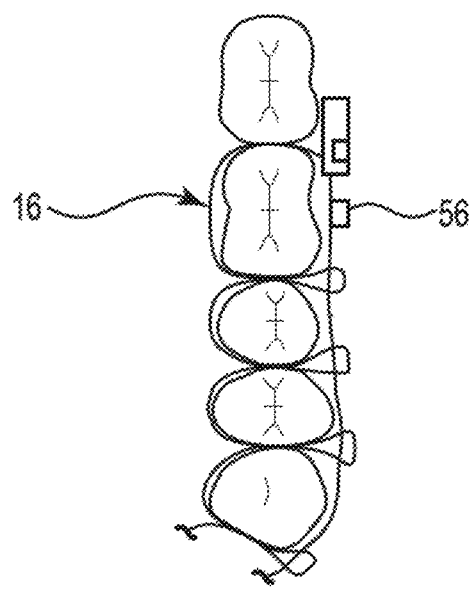
FIG. 10 is a top view of the maxillomandibular fixation device of FIG. 9.
Figure 11:
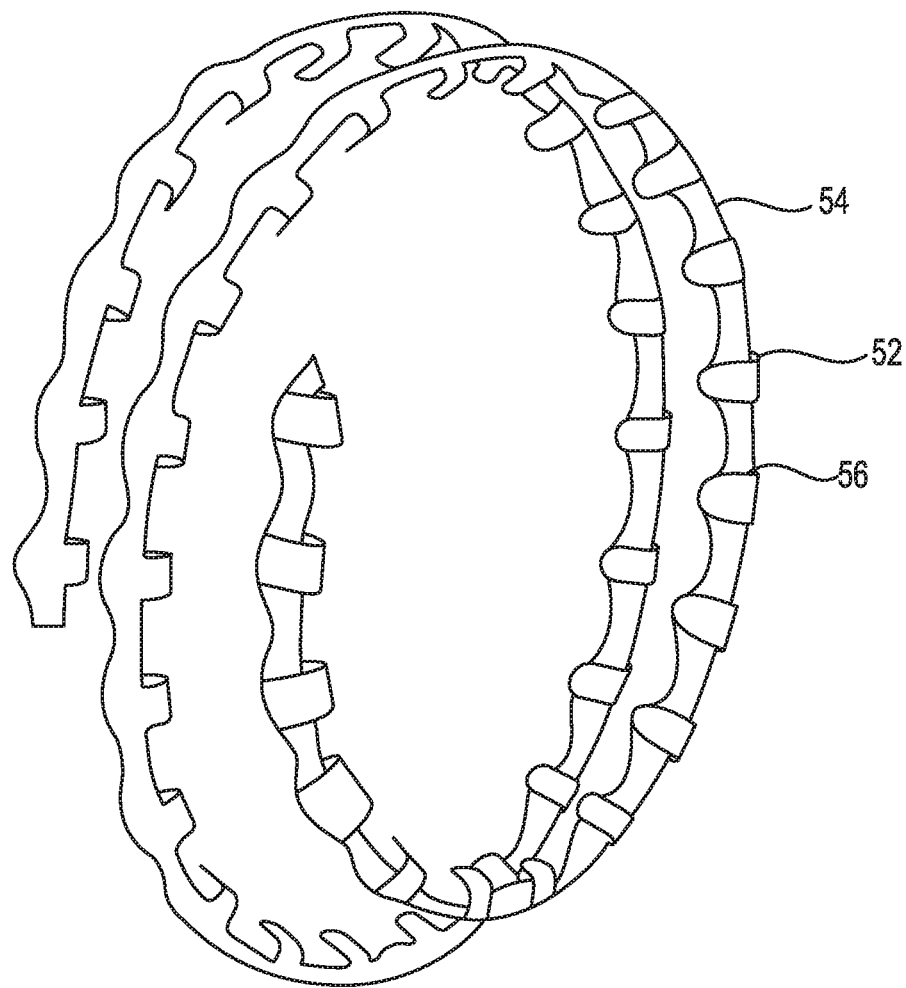
FIG. 11 is a perspective view of an arch bar in accordance with one aspect of the invention that receives a slide clamp assembly.

Referring now to FIGS. 9-11 another aspect of a maxillomandibular fixation device will now be described. The material 16 construct as described above is weaved in and out, between the teeth as best seen in FIG. 10. The embrasure space will be entered from the occlusal aspect, avoiding necrosis of the dental papilla as well as greatly speeding up the placement. Referring now to FIGS. 9 and 10, the strip of material 16 is secured in place with a single slide clamp assembly 50 slidably received by arch bar 52 best seen in FIGS. 9 and 10. Arch bar 52, as seen in FIG. 11, includes a body 54 and one or more hooks 56 and is approximately 10-14 cm in length and 2-3 mm in width. Hooks 56 receives wires 134 for wiring the jaw closed during the healing process. The slide clamp assembly 50 includes an aperture therethrough for receiving material 16. The slide clamp assembly 50 also includes a channel for receiving the arch bar body 54 and an aperture for receiving the material 16. Slide clamp assembly 50, when slidingly clamped in place, will secure and lock the strip of material 16 by a compression fit to the arch bar 52. The arch bar 52 of FIG. 11 will have been adapted along the buccal aspect of the alveolar arches.

Referring now to FIGS. 12-14 another aspect of a maxillomandibular fixation device will now be described. Clamping assembly 100 is generally square-shaped although those of skill in the art will appreciated any generally square, oval or rectangular shape may be used. Clamping assembly 100 includes body 110, top opening 112, bottom opening 114 and side openings 116. Side openings 116 receive arch bar 52 as seen in FIG. 11. Clamping assembly 100 includes insert 118 having a main body portion 120 insertable into an interior 111 the clamping assembly body 110. Main body portion 120 includes one or more ratcheting surfaces 122 on a side thereof, top portion 124 and hook 126. When insert 118 is inserted into the interior 111 of clamping assembly body 110 it extends through the top opening 112 to secure it in place. Those of skill in the art will appreciate however that top opening 112 may be eliminated and the insert 118 is simply received within interior 111 in a friction fit relationship. One or more ratcheting surfaces 122 engage one or more mating ratcheting surfaces 123 on the interior 111 of the clamping assembly body 110.

Figure 13A:
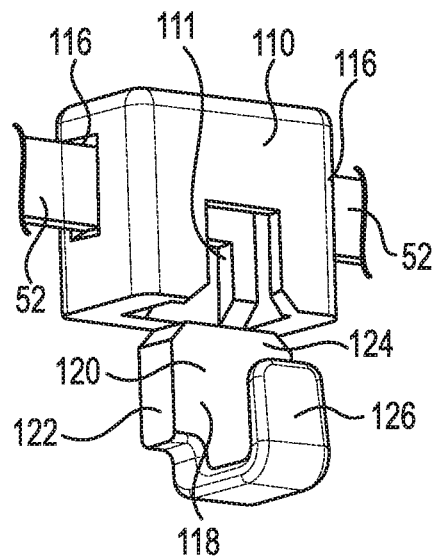
FIG. 13A is a perspective view of the clamping assembly of FIG. 12 showing the insert with ratcheting surface.
Figure 13B:
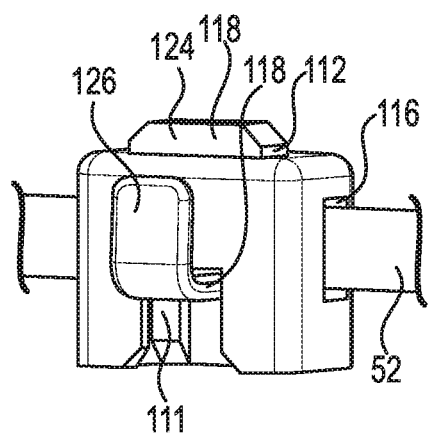
FIG. 13B is a perspective view of the clamping assembly of FIG. 12 showing the insert inserted into the body of the clamping assembly.
Figure 13C:
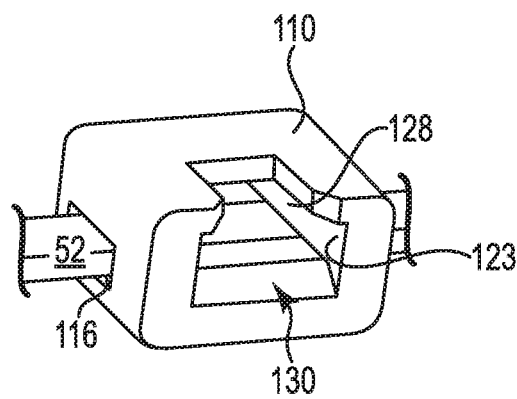
FIGS. 13C-D are alternative views of the interior of the body of the clamping assembly of FIG. 12.
Figure 13D:
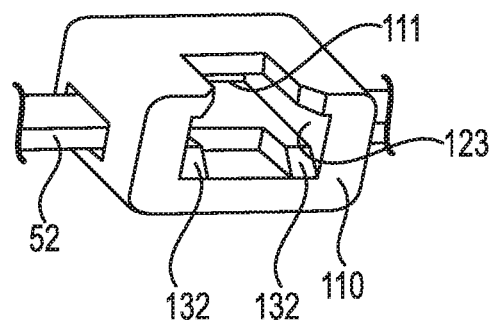

As best seen in FIGS. 13C, the interior of clamping assembly body 110 includes a shelf 130 that extends from one interior side wall 128 to another. Shelf 130 exerts compression on insert 118 prior to it being fully inserted into body 110 to ensure it is not jarred lose and becomes lost. Alternatively, as seen in FIG. 13D a pair of steps 132 extend outwardly from the interior side walls 128 but do not cross the entire width of interior 111. Similar to shelf 130, pair of steps 132 exert compression on insert 118 prior to it being fully inserted into body 110 to ensure it is not jarred lose and becomes lost.

Figure 14A:
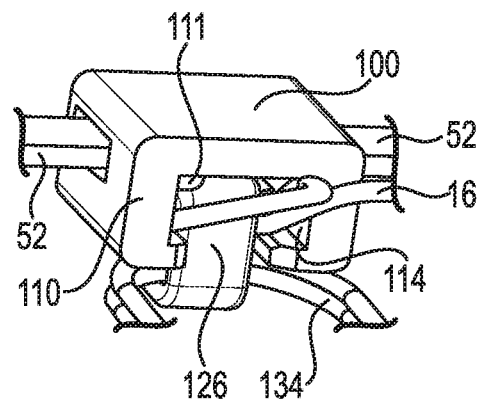
FIGS. 14A-B show the strip of material positioned around the insert hook being inserted into the opening in the clamping assembly body.
Figure 14B:
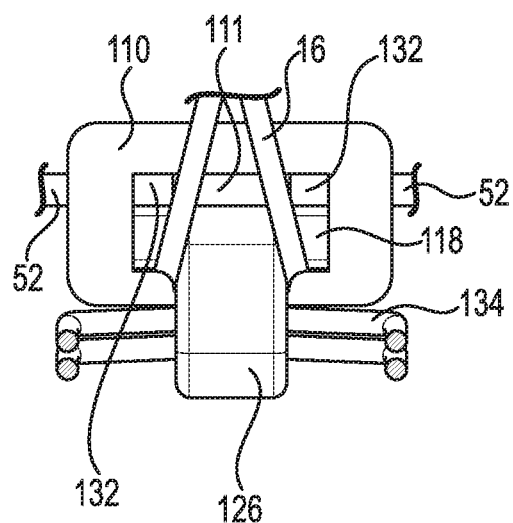

Referring now to FIGS. 14A-B the operation of clamping assembly body 110 is depicted. A single strip of material 16 is positioned over hook 126. Slight force is exerted on insert 118 to insert it into the interior 111 of clamping assembly body 110. The top portion 124 of insert 118 fits through top opening 112 while the one or more insert ratcheting surfaces 122 mate with the clamping assembly body ratcheting surface 123 to secure or pinch the strip of material 16 securely in position within interior 111, as best seen in FIG. 14B.

Figure 15:
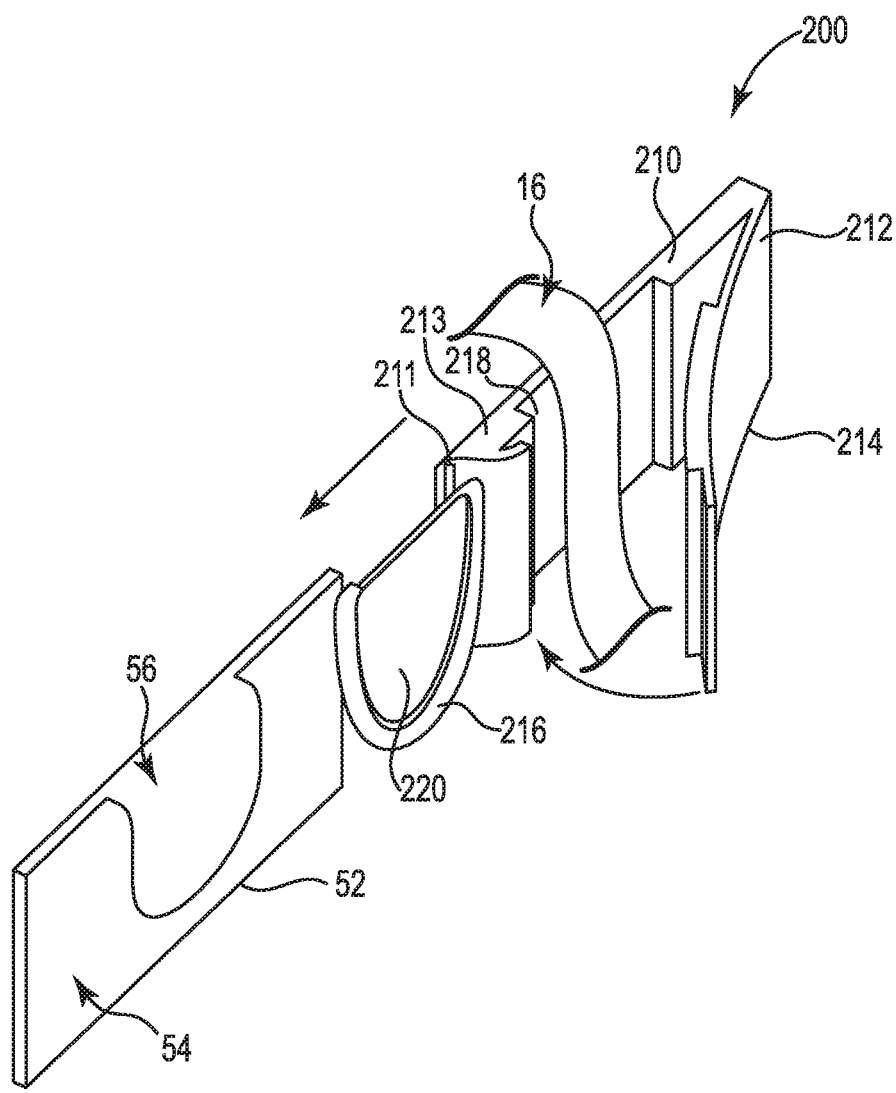
FIG. 15 is a perspective view of another aspect of the clamping assembly in accordance with the invention showing a side lever that secures the strip of material into position.

Referring now to FIG. 15 another aspect of a clamping assembly 200 is depicted. Clamping assembly 200 includes base 210, side clamp 212 with lever 214 and laterally extending projection 216. Base 210 includes a slight indentation 218 for receiving strip of material 16. Those of skill in the art will appreciate however that indentation 218 may be eliminated and the base 210 receives strip of material 16. Base 210 includes a channel 211 on a back side 213 thereof that slides onto and is received by the body 54 of arch bar 52. Side clamp includes a lever 214 that moves from a first position to a second position that fits into indentation 218 or abuts base 210 to secure strip of material 16 therein. Laterally extending projection 216 is generally U-shaped and defines U-shaped space 220. In operation, the channel 211 of base 210 slides onto and is received by body 54 of arch bar 52. The U-shaped space 220 of laterally extending projection 216 is matingly received by hook 56 in a snap-fit relationship to secure clamping assembly 200 onto the arch bar 52.

Figure 16A:
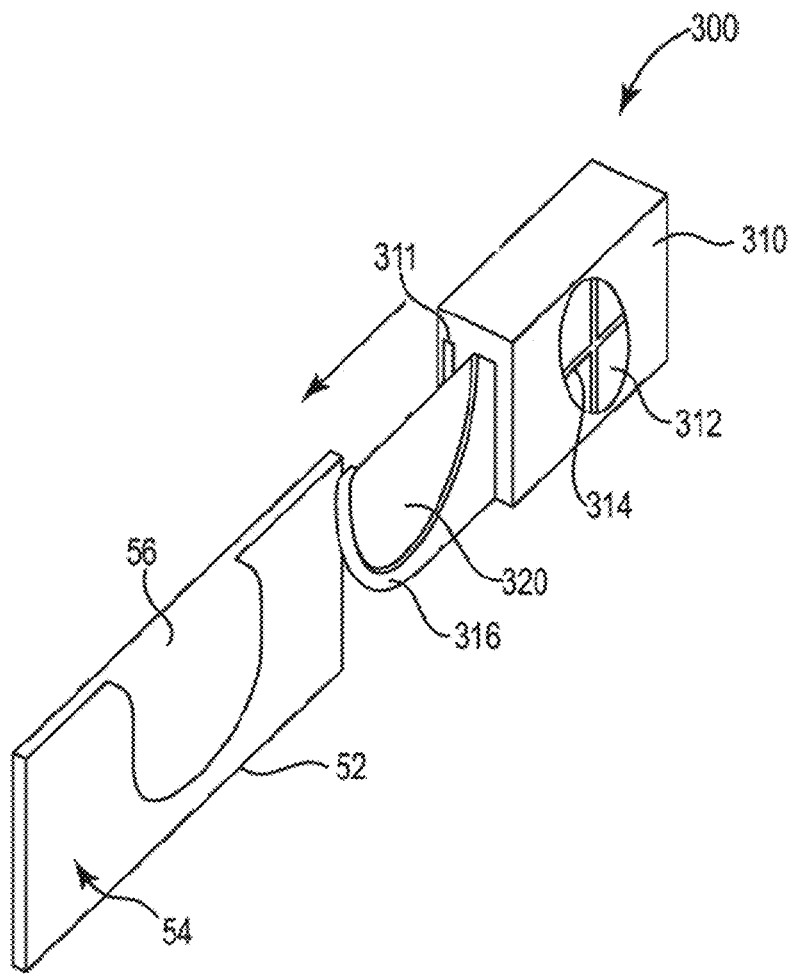
FIGS. 16A-B are perspective views of another aspect of the clamping assembly in accordance with the invention showing a spool for securing the strip of material inserted into the body of the clamping assembly and the backside of the body of the clamping assembly.
Figure 16B:
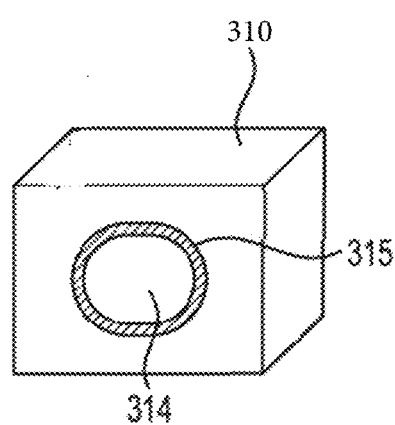
Figure 17A:
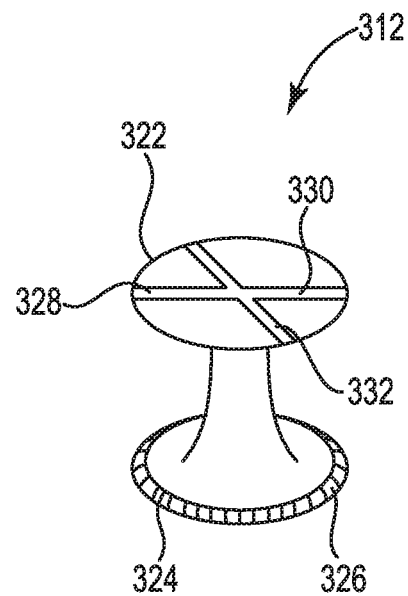
FIGS. 17A-B are a perspective view and a side view, respectively, of the spool depicted in FIG. 16A with detail thereof.
Figure 17B:
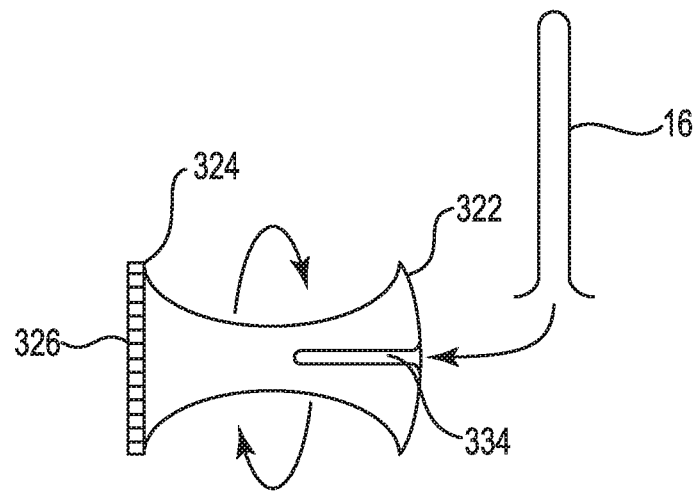

Referring now to FIGS. 16-17 another aspect of a clamping assembly 300 is depicted. Clamping assembly 300 includes base 310, spool 312 and laterally extending projection 316. Base 310 includes an opening 314 therethrough for receiving spool 312. The backside of opening 314 includes a ratcheting surface 315 extending wholly or partially around a circumference thereof. Laterally extending projection 316 is generally U-shaped and defines U-shaped space 320. Spool 312 includes a first flared end 322 and a second flared end 324 including a narrowed region 318 extending therebetween. Spool 312 includes a ratcheting surface 326 on the bottom portion 324 that mates wholly or partially with the ratcheting surface 315 on the backside of opening 314 as best seen in FIG. 16A.

As best seen in FIG. 17, the first flared end 322 of spool 312 includes a cruciform 328 having two legs 330, 332 for rotatably receiving a screwdriver. The intersection of legs 330, 332 is cut through the narrowed region 318 to form channel 334. Channel 334 receives strip of material 16. Those of skill in the art will appreciate, however, that there may be only one leg that receives a screwdriver, a portion of which is cut through the narrowed region 318 to form channel 334.

In operation, the channel 311 of base 310 slides onto and is received by body 54 of arch bar 52. The U-shaped space 320 of laterally extending projection 316 is matingly received by hook 56 in a snap-fit relationship to secure clamping assembly 300 onto the arch bar 52. The surgeon inserts strip of material 16 into channel 334 and wraps the strip of material 16 one or more turns to get it started around narrowed region 318. The spool is inserted into opening 314 of base 310 until the ratcheting surface 326 mates with the ratcheting surface 315 on the backside of opening 314. Using a screwdriver or other tool inserted into legs 328, 330 (or a single leg) the surgeon turns the spool until the strip of material 16 is taut and securely wound around narrowed region 318. Ratcheting surfaces 315, 326 hold the strip of material securely in place.

Base 210 and 310 may optionally include a hook (not shown) thereon similar to hook 56 such that when the jaw is wired closed with wire 134, wire 134 can extend and be secured to the clamping assembly 200, 300.

Those of skill in the art will appreciate that the maxillomandibular fixation devices describe herein will dramatically reduce the time needed to place the patient in maxillomandibular fixation as well as improve the stability. The present technique may also reduce the morbidity associated with conventional surgical techniques and devices. In addition, removing the maxillomandibular fixation will be much faster and not require sedation or surgery. Rather, the placement and removal may easily done in an office setting.

While the invention has been particularly shown and described, those of ordinary skill in the art will appreciate and understand that changes in form and details

What is claimed is:

1. A maxillomandibular fixation device comprising:
   a single strip of material for positioning around multiple teeth of an individual;
   an arch bar, and
   a clamping assembly for securing the single strip of material, the clamping assembly comprising a base coupled to the arch bar,
   wherein the arch bar comprises a plurality of hooks configured such that the single strip of material when weaved around one or more of the multiple teeth attaches to at least some of the plurality of hooks for anchoring the arch bar against the multiple teeth,
   wherein the base of the clamping assembly comprises an opening extending therethrough,
   wherein the maxillomandibular fixation device further comprises a spool received within the opening.

2. The maxillomandibular fixation device of claim 1, wherein a first end of the spool includes one or more legs, said one or more legs defining a channel for receiving a portion of the strip of material.

3. The maxillomandibular fixation device of claim 1, wherein a second end of the spool includes a first ratcheting surface matingly received by a second ratcheting surface included within the base opening.

4. The maxillomandibular fixation device of claim 1, wherein the opening includes a ratcheting surface wholly or partially extending around a circumference thereof.

5. The maxillomandibular fixation device of claim 1, wherein the single strip of material is configured to be weaved around a tooth of the multiple teeth and cross a gap between the tooth and an adjacent tooth at least twice for attaching to one of the plurality of hooks.

6. The maxillomandibular fixation device of 1, wherein the arch bar further comprises an arm extending downwardly therefrom and configured to be placed in edentulous areas.

7. The maxillomandibular fixation device of claim 6, wherein the arm comprises an aperture for receiving fastening means for fastening the arm to an alveolar bone.

8. The maxillomandibular fixation device of claim 7, wherein the fastening means comprises a bone screw.

9. The maxillomandibular fixation device of claim 1, wherein the strip of material is selected from an aramid, an ultra high-density polyethylene and a metal.

10. The maxillomandibular fixation device of claim 9, wherein the aramid is poly-para-phenylene terephthalamide.

11. The maxillomandibular fixation device of claim 9, wherein the metal is stainless steel.

12. The maxillomandibular fixation device of claim 1, wherein the single strip of material is 45 cm to 50 cm in length.

13. The maxillomandibular fixation device of claim 1, wherein the single strip of material is 3 cm to 4 cm in length.

14. The maxillomandibular fixation device of claim 1, wherein the clamping assembly is constructed of stainless steel or titanium.

15. A maxillomandibular fixation device comprising:
   a single strip of material for positioning around multiple teeth of an individual;
   an arch bar; and
   a clamping assembly comprising a base coupled to the arch bar,
   wherein the arch bar comprises a plurality of hooks configured such that the single strip of material when weaved around one or more of the multiple teeth attaches to at least some of the plurality of hooks for anchoring the arch bar against the multiple teeth, and the base further comprises a laterally extending U-shaped projection defining a U-shaped space.

16. The maxillomandibular fixation device of claim 15, wherein the arch bar comprises a hook that matingly receives the U-shaped space in a snap fit relationship.

* * * * *